United States Patent
Dellock et al.

(10) Patent No.: US 10,363,326 B2
(45) Date of Patent: Jul. 30, 2019

(54) SELF-CLEANING SENSOR SURFACE

(71) Applicant: Ford Global Technologies, LLC, Dearborn, MI (US)

(72) Inventors: Paul Kenneth Dellock, Northville, MI (US); Stuart C. Salter, White Lake, MI (US); Harry Lobo, Canton, MI (US); Venkatesh Krishnan, Canton, MI (US); Pietro Buttolo, Dearborn Heights, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 41 days.

(21) Appl. No.: 15/647,795

(22) Filed: Jul. 12, 2017

(65) Prior Publication Data

US 2019/0015536 A1 Jan. 17, 2019

(51) Int. Cl.
*A61L 2/26* (2006.01)
*A61L 2/10* (2006.01)
*B60Q 1/00* (2006.01)

(52) U.S. Cl.
CPC ........ *A61L 2/10* (2013.01); *A61L 2/26* (2013.01); *B60Q 1/0023* (2013.01); *A61L 2202/20* (2013.01)

(58) Field of Classification Search
CPC ............ A61L 2/10; A61L 2/26; B60Q 1/0023
See application file for complete search history.

(56) References Cited

U.S. PATENT DOCUMENTS 8,147,971 B2 4/2012 Van Herpen
2006/0152705 A1 7/2006 Yoshida et al.

FOREIGN PATENT DOCUMENTS

| DE | 102007059758 A1 | 6/2009 |
| JP | 4885746 B2 | 12/2011 |
| JP | 2014215418 A | 11/2014 |
| WO | WO 9723572 A1 | 7/1997 |

*Primary Examiner* — Sean E Conley
(74) *Attorney, Agent, or Firm* — Frank A. MacKenzie; Bejin Bieneman PLC

(57) ABSTRACT

A computing device in a vehicle can be programmed to activate a self-cleaning glass surface by irradiating the self-cleaning glass surface with LED ultraviolet radiation based on a determined energy of external ultraviolet radiation and a schedule. The computing device can activate a self-cleaning glass surface by irradiating the self-cleaning glass surface with LED ultraviolet radiation based on determining an optical state of the self-cleaning glass.

10 Claims, 5 Drawing Sheets

SELF-CLEANING SENSOR SURFACE

BACKGROUND

Vehicles can be equipped to operate in both autonomous and occupant piloted mode. Vehicles can be equipped with computing devices, networks, sensors and controllers to acquire information regarding the vehicle's environment and to pilot the vehicle based on the information. Safe and comfortable piloting of the vehicle can depend upon acquiring accurate and timely information regarding the vehicles' environment. Computing devices, networks, sensors and controllers can be equipped to analyze their performance, detect when information is not being acquired in an accurate and timely fashion, and take corrective actions including informing an occupant of the vehicle, relinquishing autonomous control or parking the vehicle.

DETAILED DESCRIPTION

Figure 1:
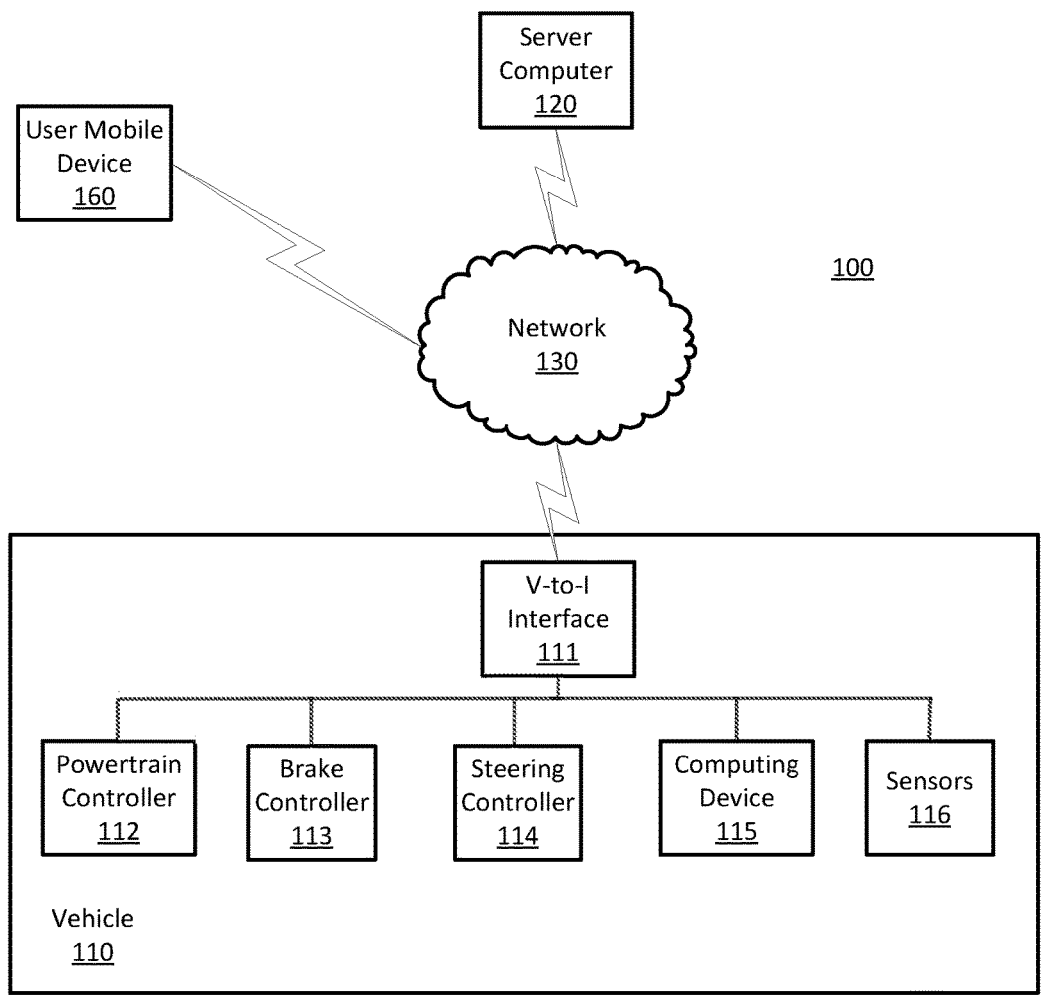
FIG. 1 is a block diagram of an example vehicle.

Vehicles can be equipped to operate in both autonomous and occupant piloted mode. By a semi- or fully-autonomous mode, we mean a mode of operation wherein a vehicle can be piloted by a computing device as part of a vehicle information system having sensors and controllers. The vehicle can be occupied or unoccupied, but in either case the vehicle can be piloted without assistance of an occupant. For purposes of this disclosure, an autonomous mode is defined as one in which each of vehicle propulsion (e.g., via a powertrain including an internal combustion engine and/or electric motor), braking, and steering are controlled by one or more vehicle computers; in a semi-autonomous mode the vehicle computer(s) control(s) one or two of vehicle propulsion, braking, and steering.

Disclosed herein is a method, comprising: activating a self-cleaning glass surface by irradiating the self-cleaning glass surface with UV LED radiation based on determined environmental UV radiation energy and a schedule. The UV LED radiation can be further based on a determined optical state of the self-cleaning glass. The optical state of the self-cleaning glass can be determined by determining an IR reflectance of the self-cleaning glass, wherein the UV LED radiation includes a wavelength of 365 nanometers and wherein the UV LED radiation has an energy of greater than 1 W/cm$^2$. The schedule can be based on expected environmental UV radiation. Determining external UV radiation can be based on estimating W*sec/cm$^2$ of UV radiation energy on the self-cleaning glass per time period, wherein the self-cleaning glass is coated with an optical UV coating.

The schedule can include less than ½ hour of UV LED radiation, wherein the less than ½ hour of UV LED radiation activates the self-cleaning glass surface for at least 2 to 5 hours. Estimating W*sec/cm$^2$ of ultraviolet energy on the self-cleaning glass surface per time period includes acquiring data regarding environmental UV radiation energy, wherein a UV LED "on" time is based on the acquired data regarding environmental UV radiation energy and the schedule. A location history for a vehicle can be determined, and a self-cleaning glass surface can be activated by irradiating the self-cleaning glass surface with UV LED radiation based on the location history, wherein a UV LED "on" time is based on the acquired data regarding environmental UV radiation energy, the schedule, and the location history.

Further disclosed is a computer readable medium storing program instructions for executing some or all of the above method steps. Further disclosed is a computer programmed for executing some or all of the above method steps, including a computer apparatus, programmed to activate a self-cleaning glass surface by irradiating the self-cleaning glass surface with UV LED radiation based on determined environmental UV radiation energy and a schedule. The computer apparatus can be further programmed to determine the UV LED radiation based on a determined optical state of the self-cleaning glass. The optical state of the self-cleaning glass can be determined by determining an IR reflectance of the self-cleaning glass, wherein the UV LED radiation includes a wavelength of 365 nanometers and wherein the UV LED radiation has an energy of greater than 1 W/cm$^2$. The schedule can be based on expected environmental UV radiation. Determining external UV radiation can be based on estimating W*sec/cm$^2$ of UV radiation energy on the self-cleaning glass per time period, wherein the self-cleaning glass is coated with an optical UV coating.

The computer apparatus can be further programmed to determine the schedule that can include less than ½ hour of UV LED radiation, wherein the less than ½ hour of UV LED radiation activates the self-cleaning glass surface for at least 2 to 5 hours. Estimating W*sec/cm$^2$ of ultraviolet energy on the self-cleaning glass surface per time period includes acquiring data regarding environmental UV radiation energy, wherein a UV LED "on" time is based on the acquired data regarding environmental UV radiation energy and the schedule. The computer apparatus can be further programmed to determine a location history for a vehicle, and a self-cleaning glass surface can be activated by irradiating the self-cleaning glass surface with UV LED radiation based on the location history, wherein a UV LED "on" time is based on the acquired data regarding environmental UV radiation energy, the schedule, and the location history.

FIG. 1 is a diagram of a vehicle information system 100 that includes a vehicle 110 operable in autonomous ("autonomous" by itself in this disclosure means "fully autonomous") and occupant piloted (also referred to as non-autonomous) mode in accordance with disclosed implementations. Vehicle 110 also includes one or more computing devices 115 for performing computations for piloting the vehicle 110 during autonomous operation. Computing devices 115 can receive information regarding the operation of the vehicle from sensors 116.

The computing device 115 includes a processor and a memory such as are known. Further, the memory includes one or more forms of computer-readable media, and stores instructions executable by the processor for performing various operations, including as disclosed herein. For example, the computing device 115 may include programming to operate one or more of vehicle brakes, propulsion (e.g., control of acceleration in the vehicle 110 by controlling one or more of an internal combustion engine, electric motor, hybrid engine, etc.), steering, climate control, interior and/or exterior lights, etc., as well as to determine whether and when the computing device 115, as opposed to a human operator, is to control such operations.

The computing device 115 may include or be communicatively coupled to, e.g., via a vehicle communications bus as described further below, more than one computing devices, e.g., controllers or the like included in the vehicle 110 for monitoring and/or controlling various vehicle components, e.g., a powertrain controller 112, a brake controller 113, a steering controller 114, etc. The computing device 115 is generally arranged for communications on a vehicle communication network such as a bus in the vehicle 110 such as a controller area network (CAN) or the like; the vehicle 110 network can include wired or wireless communication mechanism such as are known, e.g., Ethernet or other communication protocols.

Via the vehicle network, the computing device 115 may transmit messages to various devices in the vehicle and/or receive messages from the various devices, e.g., controllers, actuators, sensors, etc., including sensors 116. Alternatively, or additionally, in cases where the computing device 115 actually comprises multiple devices, the vehicle communication network may be used for communications between devices represented as the computing device 115 in this disclosure. Further, as mentioned below, various controllers or sensing elements may provide data to the computing device 115 via the vehicle communication network.

In addition, the computing device 115 may be configured for communicating through a vehicle-to-infrastructure (V-to-I) interface 111 with a remote server computer 120, e.g., a cloud server, via a network 130, which, as described below, may utilize various wired and/or wireless networking technologies, e.g., cellular, BLUETOOTH® and wired and/or wireless packet networks. Computing device 115 may be configured for communicating with other vehicles 110 through V-to-I interface 111 using vehicle-to-vehicle (V-to-V) networks formed on an ad hoc basis among nearby vehicles 110 or formed through infrastructure-based networks. The computing device 115 also includes nonvolatile memory such as is known. Computing device 115 can log information by storing the information in nonvolatile memory for later retrieval and transmittal via the vehicle communication network and a vehicle to infrastructure (V-to-I) interface 111 to a server computer 120 or user mobile device 160.

As already mentioned, generally included in instructions stored in the memory and executed by the processor of the computing device 115 is programming for operating one or more vehicle 110 components, e.g., braking, steering, propulsion, etc., without intervention of a human operator. Using data received in the computing device 115, e.g., the sensor data from the sensors 116, the server computer 120, etc., the computing device 115 may make various determinations and/or control various vehicle 110 components and/or operations without a driver to operate the vehicle 110. For example, the computing device 115 may include programming to regulate vehicle 110 operational behaviors such as speed, acceleration, deceleration, steering, etc., as well as tactical behaviors such as a distance between vehicles and/or amount of time between vehicles, lane-change, minimum gap between vehicles, left-turn-across-path minimum, time-to-arrival at a particular location and intersection (without signal) minimum time-to-arrival to cross the intersection.

Controllers, as that term is used herein, include computing devices that typically are programmed to control a specific vehicle subsystem. Examples include a powertrain controller 112, a brake controller 113, and a steering controller 114. A controller may be an electronic control unit (ECU) such as is known, possibly including additional programming as described herein. The controllers may communicatively be connected to and receive instructions from the computing device 115 to actuate the subsystem according to the instructions. For example, the brake controller 113 may receive instructions from the computing device 115 to operate the brakes of the vehicle 110.

The one or more controllers 112, 113, 114 for the vehicle 110 may include known electronic control units (ECUs) or the like including, as non-limiting examples, one or more powertrain controllers 112, one or more brake controllers 113 and one or more steering controllers 114. Each of the controllers 112, 113, 114 may include respective processors and memories and one or more actuators. The controllers 112, 113, 114 may be programmed and connected to a vehicle 110 communications bus, such as a controller area network (CAN) bus or local interconnect network (LIN) bus, to receive instructions from the computer 115 and control actuators based on the instructions.

Sensors 116 may include a variety of devices known to provide data via the vehicle communications bus. For example, a radar fixed to a front bumper (not shown) of the vehicle 110 may provide a distance from the vehicle 110 to a next vehicle in front of the vehicle 110, or a global positioning system (GPS) sensor disposed in the vehicle 110 may provide geographical coordinates of the vehicle 110. The distance(s) provided by the radar and/or other sensors 116 and/or the geographical coordinates provided by the GPS sensor may be used by the computing device 115 to operate the vehicle 110 autonomously or semi-autonomously.

The vehicle 110 is generally a land-based autonomous vehicle 110 having three or more wheels, e.g., a passenger car, light truck, etc. The vehicle 110 includes one or more sensors 116, the V-to-I interface 111, the computing device 115 and one or more controllers 112, 113, 114.

The sensors 116 may be programmed to collect data related to the vehicle 110 and the environment in which the vehicle 110 is operating. By way of example, and not limitation, sensors 116 may include, e.g., altimeters, cameras, LIDAR, radar, ultrasonic sensors, infrared sensors, pressure sensors, accelerometers, gyroscopes, temperature sensors, pressure sensors, hall sensors, optical sensors, voltage sensors, current sensors, mechanical sensors such as switches, etc. The sensors 116 may be used to sense the environment in which the vehicle 110 is operating such as weather conditions, the grade of a road, the location of a road or locations of neighboring vehicles 110. The sensors 116 may further be used to collect data including dynamic vehicle 110 data related to operations of the vehicle 110 such as velocity, yaw rate, steering angle, engine speed, brake pressure, oil pressure, the power level applied to controllers 112, 113, 114 in the vehicle 110, connectivity between components and electrical and logical health of the vehicle 110.

Figure 2:
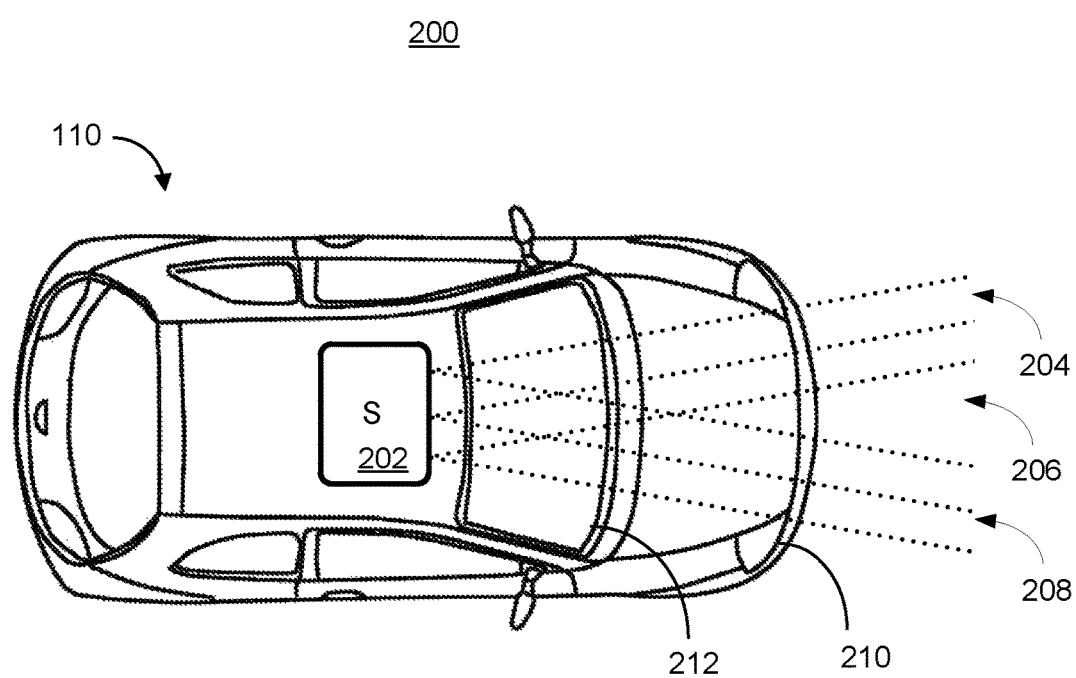
FIG. 2 is a diagram of an example vehicle with a sensor pod.

FIG. 2 is a diagram of traffic scene 200 including a top-down view of vehicle 110 having a sensor pod 202 (marked "S") attached to a roof portion of vehicle 110. The sensor pod 202 is a container, e.g., including a housing or the like within which sensors 116 can be disposed, that includes sensors 116 that can acquire data from and/or about the environment in which vehicle 110 is operating. Fields of view 204, 206, 208 (dotted lines) of three example sensors 116 included in sensor pod 202 are shown in traffic scene 200. The three example sensors 116 can include video, infrared video, and LIDAR sensors 116 for example. The sensors 116 can be configured in a sensor pod 202, attached or otherwise mounted on a roof portion of vehicle 110 in order to provide sensors 116 with maximum possible fields of view 204, 206, 208 of the environment in which vehicle 110 operates. Traffic scene 200 shows a sensor pod 202 with fields of view 204, 206, 208 directed forward in the direction of travel of vehicle 110, however, sensor pod 202 can have sensor 116 with fields of view 204, 206, 208 directed to the rear or to the sides of vehicle 110.

In other cases, one or more sensors 116 can be included behind sealed glass portions of headlight 210 or windshield 212 of vehicle 110, where glass is defined as silicon-based glass, glass-like plastic, or glass composite material that can include glass and other materials (e.g. safety glass) that is transparent to visible light. A portion of sensor pod 202, a cover portion of headlight 210, and windshield 212 can be transparent with respect to the wavelengths of light employed by sensors 116 including visible wavelengths. Glass portions of sensor pod 202, headlight 210 or windshield 212 can be sealed to prevent exposure of sensors 116 to the environment, for example.

Configuring sensors 116 behind sealed glass portions of vehicle 110 and sensor pod 202 protects sensors 116 from harsh environments, but can present issues with respect to degradation in visibility through the glass caused by environmental elements such as dirt and water droplets accumulating on the glass, for example. Visibility is defined as the percent transmission of light over selected bands of wavelengths. A vehicle 110 windshield 212 can present the same issues with respect to degradation in visibility. Since an occupant can depend upon visibility through the windshield 212 to pilot vehicle 110, windshield 212 and other windows or glass surfaces can be equipped with washer fluid spray nozzles and windshield wipers to maintain visibility. Since sensors 116 configured behind sealed glass portions of vehicle 110 and sensor pod 202 can also depend upon visibility through glass to accurately and reliably acquire information, the sealed glass portions can be similarly equipped with washer fluid spray nozzles and wipers to maintain visibility.

Equipping sealed glass portions of vehicle 110 and sensor pod 202 with washer fluid spray nozzles and wipers can clean accumulated dirt from sealed glass portions of vehicle 110 and sensor pod 202, but represent significant additional cost, present difficulties in routing washer fluid from large, remote reservoirs and can be viewed as aesthetically displeasing by occupants. Cleaning sealed glass portions of vehicle 110 can result in dripping water on portions of vehicle 110 and sensor pod 202 that can also be viewed as aesthetically displeasing. Washer fluid spray nozzles and wipers can have difficulty cleaning oil-based dirt, such as found on road surfaces, and, in spite of washer fluid spray nozzles and wipers, during heavy rain, water can bead on the surface and reduce visibility because the glass can be hydrophobic.

Figure 3:
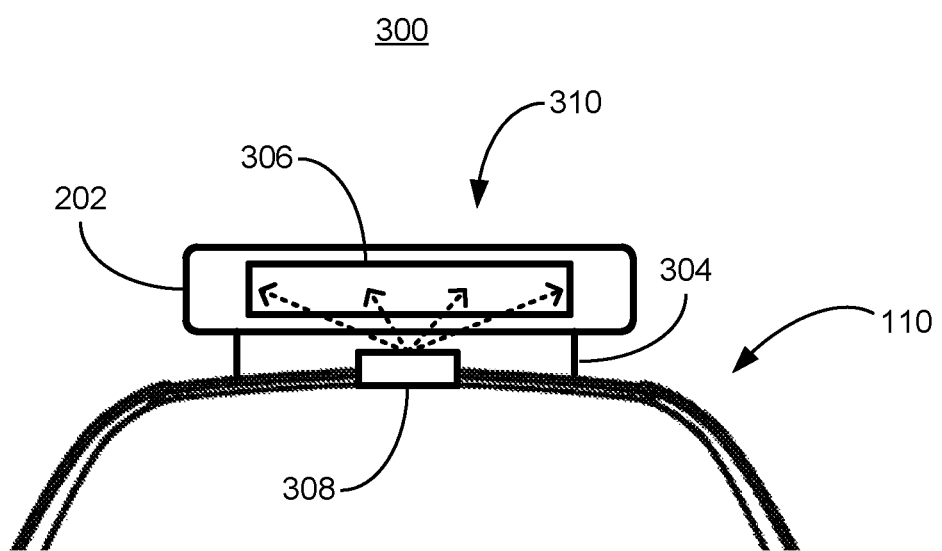
FIG. 3 is a diagram of an example vehicle with a sensor pod.

FIG. 3 is a traffic scene 300 showing a front view of a roof portion of a vehicle 110 equipped with sensor pod 202 operatively mounted on a roof portion of vehicle 110 by mount 304. In other cases, sensor pod 202 can be mounted on a roof portion of vehicle 110 directly, without a mount 304. Sensor pod 202 is equipped with sealed glass portion 306 behind which are configured sensors 116. Sealed glass portion 306 of sensor pod 202 can be constructed using self-cleaning glass. "Self-cleaning" glass in the context of this disclosure means glass or glass-like plastic, for example, that can be modified with a surface coating that can be activated to shed dirt or debris without assistance by devices such as spray nozzles and wipers. Self-cleaning glass can be manufactured to include a surface coating of titanium dioxide ($TIO^2$). $TIO^2$ is a photo-catalyst that promotes chemical reactions on the surface of the glass in response to exposure to ultraviolet (UV) radiation or light with a wavelength less than 387 nanometers (nm) in the UV wavelength range and an energy of at least 1 milliwatt/centimeter (mW/cm). UV light can cause $TIO^2$ to release electrons that interact with water molecules to create hydroxyl radicals (OH—). The OH— radical attacks carbon-based molecules in dirt particles adhering to the surface of the self-cleaning glass in a chemical reaction called "cracking", where carbon-carbon chemical bonds are broken in long-chain hydrocarbon molecules, breaking them apart until the organic portions of the dirt becomes simple hydrocarbons, carbon dioxide and water. Cracking long-chain hydrocarbon molecules dissolves the surface of the dirt particle adhering to the cleaning the self-cleaning glass, thereby permitting the self-cleaning glass to easily shed the dirt particle. The OH— radical can also make the self-cleaning glass hydrophilic, and thereby prevent water from beading on the self-cleaning glass during heavy rain. Although the self-cleaning glass may need to be occasionally washed, oils, pollutants and other organic substances will not stick to the self-cleaning glass since they have been attacked by hydroxyl radicals and will be easily washed away.

Self-cleaning glass is activated by exposure to UV radiation with a wavelength less than 387 nm and an energy of at least 1 $mW/cm^2$ for a period of time based on the energy of absorbed UV radiation. By activated we mean that the $TIO^2$ in the self-cleaning glass has absorbed enough energy to promote chemical reactions. The time required for activation is proportional to the amount of supplied UV radiation in $mW/cm^2$. Direct sunlight supplies a maximum $mW/cm^2$ of UV radiation while cloudy, diffuse sunlight supplies much fewer $mW/cm^2$ of UV radiation and the night sky supplies essentially no $mW/cm^2$ of UV radiation. For example, at middle latitudes in summer at midday on a clear day, sunlight can supply up to 3.5 $mW/cm^2$ of UV light energy. Reduction in UV light energy on cloudy days is proportional to the reduction in overall sunlight. Self-cleaning glass can therefore take much longer to activate on cloudy days than on sunny days, if the amount or UV radiation reaching the self-cleaning glass exceeds 1 $mW/cm^2$. If the amount of UV radiation reaching the self-cleaning glass does not exceed 1 $mW/cm^2$ for a minimum amount of time, the self-cleaning glass will not activate, nor does the self-cleaning glass activate at night. Once activated, self-cleaning glass can remain active to two to five hours without further supplied UV light energy.

Self-cleaning glass can be supplied with UV radiation from man-made radiation sources to activate self-cleaning glass in the absence of naturally occurring sunlight. FIG. 3 shows a UV light emitter 308, configured to emit UV LED radiation 310 (dotted arrows) directed at the sealed glass portion 306 of sensor pod 202. Sensor pod 202 can be configured with sensors 116 behind sealed glass portions 306 constructed with self-cleaning glass. The sealed glass portions 306 can be configured to operate without degradation in visibility at night and on cloudy days by activating the self-cleaning glass with UV light emitter 308 having an emission wavelength of 365 nm. Energy output from UV light emitter 308 can be configured to activate self-cleaning glass in a predetermined period of time. For example, UV light emitter 308 having an output of 1 $mW/cm^2$ of UV energy can activate self-cleaning glass in about 30 minutes of radiating. Activating self-cleaning glass using artificial sources, for example UV light emitter 308, can require more time to activate than direct sunlight on sunny days, but can activate self-cleaning glass at about the same rate as partly cloudy days. In this manner, self-cleaning glass can be activated to remain clean at night and on cloudy days, in addition to sunny days.

UV light emitter 308 can include UV LEDs that emit radiation or light with wavelengths in a small (<+/−10 nm) distribution centered at 365 nm. UV light emitter 308 can be positioned outside of sensor pod 202 as shown in traffic scene 300 or inside sensor pod 202, as long as UV LEDs and incorporated optics including lenses and filters, for example, are configured so as to direct UV radiation 310 onto the sealed glass portion 306 of sensor pod 202 and thereby activate self-cleaning glass. UV LEDs with an output radiation wavelength of about 365 nm are included because about 365 nm UV LED radiation 310 is relatively harmless to humans use and they are readily available since they can be commonly used for applications such as security links, sterilization and curing adhesives, etc. 365 nm UV LED radiation 310 is generally harmless to humans since it is above a 310 nm upper limit for skin damage and below a 390 nm lower limit for eye damage.

The number of $mW/cm^2$ of UV LED radiation 310 impinging upon self-cleaning glass in sealed glass portion of sensor pod 202 from UV light emitter 308 can be predetermined to be sufficient to activate the self-cleaning glass in about ½ hour of UV LED radiation 310. Since, once activated, self-cleaning glass remains activated for 2-5 hours, UV light emitter 308 can be directed by computing device 115, for example, to radiate UV light on a regular schedule that insures that the self-cleaning glass portion of sealed glass portion 306 of sensor pod 202 remains active and therefore clean. Since the frequencies of UV light are above the frequencies of visible or IR light, most sensor 116 are unaffected by radiated UV light from UV light emitter 308. In cases where sensors 116 can be adversely affected by UV LED radiation 310 emitted by UV light emitter 308, UV light emitter can be positioned outside of sensor pod 202, as shown in traffic scene 300, and the interior surface of sealed glass portion 306 can be coated with an optical UV coating that blocks UV LED radiation 310. For example, a hindered amine like 2 ethylhexyl-p-methoxycinnamate or a similar coating can be used to block UV LED radiation 310 from UV light emitter 308 from entering interior of sensor pod 202.

Computing device 115 can determine when vehicle 110 and sensor pod 202 are exposed to environmental UV radiation from sunlight, for example, where self-cleaning glass portion of sealed glass portion 306 of sensor pod 202 can be activated or partially activated without any UV LED radiation 310 emitted by UV light emitter 308. In these cases, sensor pod 202 can be equipped with a UV light sensor operatively connected to computing device 115 to acquire data regarding the number of $mW/cm^2$ of UV radiation impinging on sealed glass portion 306 per time period that exceed 1 $mW/cm^2$, and therefore predict the level of activation of self-cleaning glass as a fraction of full activation summing the number of minutes that the UV radiation exceeded 1 $mW/cm^2$ and comparing that sum to 30, the number of minutes at 1 $mW/cm^2$ required to activate the self-cleaning glass yields the fraction of full activation. If the sum is greater than 30, the self-cleaning glass is 100% or fully activated. As described above, activation of self-cleaning glass by UV LEDs can be scheduled to maintain the self-cleaning glass in an activated state. When computing device 115 determines that a time for activation of self-cleaning glass by UV LEDs is at hand, computing device 115 can determine a predicted level of activation for the self-cleaning glass based on UV light sensor data and determine a UV LED "on" time based on the predicted fraction of full activation. If computing device 115 predicts 100% full activation, computing device 115 will not direct UV light emitter 308 to emit UV LED radiation 310, for example.

Computing device 115 can also determine the history and location of vehicle 110 when a scheduled time for activation is at hand. For example, if vehicle 110 has been garaged in an enclosed space for a period of time, although no environmental UV is available to activate the self-cleaning glass, no environmental dirt may be available to contaminate the self-cleaning glass, so less activation may be required. Computing device 115 can also determine the history and location of the vehicle 110 based on external data acquired via V-to-I interface 111 from cloud or internet sources or sensors 116 including GPS and radar. These data sources can indicate the expected environmental UV radiation available via weather reports or observations for the locations a vehicle 110 has recorded being, for example.

In other cases, computing device 115 can determine an optical state of self-cleaning glass by configuring an IR emitter and an IR receiver to form an emitter/receiver pair to emit IR radiation to be reflected off an external surface of sealed glass portion 306 of sensor pod 202 and received by the IR receiver. An optical state is defined as a measure of the amount of dirt adhering to a self-cleaning glass surface as determined by IR reflectance, e.g. an IR emitter/receiver pair. The IR emitter/receiver pair can be configured to measure IR reflectance at the surface at the critical angle of reflectance, where a large portion of the emitted IR radiation can be reflected back to the IR receiver, for example. Dirt particles adhering to the surface can change the index of refraction and thereby change the critical angle, in turn changing the percentage of IR radiation being reflected by the surface. By periodically comparing the amount of IR light reflected by an exterior portion of sealed glass portion 306 of sensor pod 202 with a previously determined and stored values, computing device 115 can determine if an external surface of sealed glass portion 306 of sensor pod 202 has dirt particles adhering and requires activation to clean. When computing device 115 determines a scheduled activation of self-cleaning glass is at hand, computing device can determine, based on periodically acquired data from an IR emitter and receiver pair, whether self-cleaning glass is dirty, and then determine whether to activate self-cleaning glass.

Returning to FIG. 2, self-cleaning glass can be included in sealed glass portions of headlight 210, windshield 212 or any other portion of the exterior of vehicle 110 that includes a sealed glass portion, such a lights or mirrors, for example. Each sealed glass portion can also include a nearby or included UV light emitter 308, to activate the self-cleaning glass portion of headlight 210, windshield 212, or any other sealed glass portion of vehicle 110. Each self-cleaning glass portion of headlight 210, windshield 212, or any other sealed glass portion of vehicle 110 can be configured with UV light sensors and IR emitter and receiver pairs that can be activated to acquire data regarding IR reflectance from a self-cleaning glass surface to estimate dirt accumulation on the self-cleaning glass. Each self-cleaning glass portion of vehicle 110 can be activated with UV LED radiation according to a schedule, wherein the schedule is modified by determined environmental (environmental UV energy), historical (vehicle 110 location) and empirical factors (IR reflectance) as described above and in relation to FIG. 3.

Figure 4:
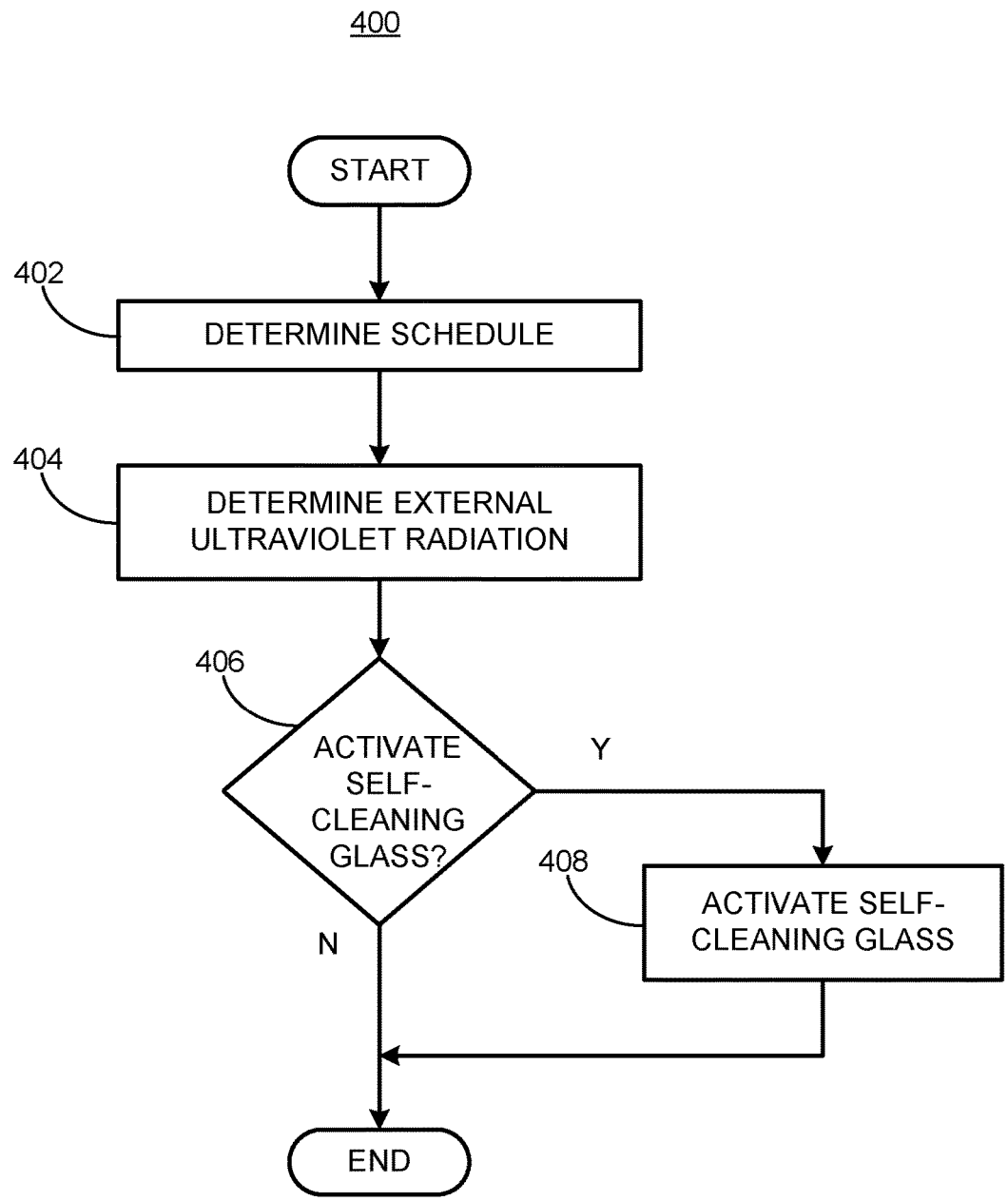
FIG. 4 is a flowchart diagram of an example process to activate self-cleaning glass.

FIG. 4 is a diagram of a flowchart, described in relation to FIGS. 1-3, of a process 400 for activating self-cleaning glass. Process 400 can be implemented by a processor of computing device 115, taking as input information from sensors 116, and executing instructions and sending control signals via controllers 112, 113, 114, for example. Process 400 includes multiple steps taken in the disclosed order. Process 400 also includes implementations including fewer steps or can include the steps taken in different orders.

Process 400 begins at step 402, where a computing device 115 in a vehicle 110 can determine a schedule for activating self-cleaning glass using UV LEDs as described above in relation to FIGS. 2 and 3, above. A step 404 computing device 115 can determine an amount of external or environmental UV radiation in mW/cm$^2$ per time period to which self-cleaning glass has been exposed to, and thereby determine a fraction of activation as described above in relation to FIG. 3. At step 406, computing device 115 can determine an amount of time to direct UV light emitter 308 to emit UV LED radiation 310 to impinge upon self-cleaning glass and thereby activate the self-cleaning glass, where the amount of time is proportional to the fraction of activation remaining. If the fraction of activation is 100% and no activation is required, the "N" branch is taken and process 400 ends. If the fraction of activation is less than 100%, the "Y" branch is taken to step 408, where the self-cleaning glass is activated by directing UV light emitter 308 to emit UV LED radiation 310 for an amount of time based on the fraction of activation. Following this step process 400 ends.

Figure 5:
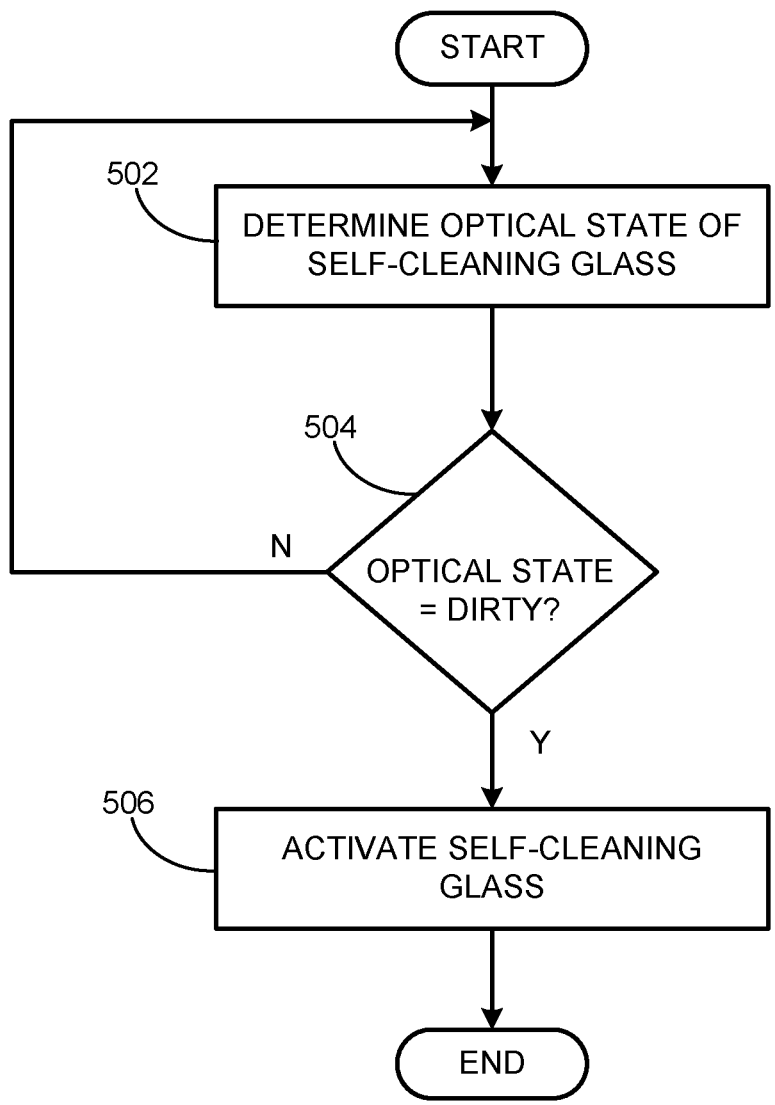
FIG. 5 is a flowchart diagram of an example process to activate self-cleaning glass.

FIG. 5 is a diagram of a flowchart, described in relation to FIGS. 1-3, of a process 500 to activate self-cleaning glass based on a determined state of the self-cleaning glass. Process 500 can be implemented by a processor of computing device 115, taking as input information from sensors 116, and executing instructions and sending control signals via controllers 112, 113, 114, for example. Process 500 includes multiple steps taken in the disclosed order. Process 500 also includes implementations including fewer steps or can include the steps taken in different orders.

Process 500 begins at step 502, where a computing device 115 in vehicle 110 can determine an optical state of self-cleaning glass portion of sealed glass portion 306 of sensor pod 202, where optical state is defined as a percentage of IR wavelength reflectance measure used to determine dirt particles adhering to self-cleaning glass. As discussed above in relation to FIG. 3, An IR emitter/receiver pair can be used to measure IR reflectance. Since dirt particles adhering to surface of self-cleaning glass can reduce IR reflectance, comparing IR reflectance values with values previously measured and stored by computing device 115 when the self-cleaning glass is known to be clean, can indicate the presence or absence of dirt particles on self-cleaning glass. Relative IR reflectance values that indicate the presence or absence of dirt particles interfering with a sensor 116 can thus be empirically determined. For one example, measured IR reflectance dropping to 90% of previously measured and stored values can indicate the presence of dirt particles adhering to a surface of self-cleaning glass.

At step 504, computing device 115 compares the determined optical state of self-cleaning glass with previously measured and stored values to determine if the optical state of self-cleaning glass is "dirty". For example, if the IR reflectance is greater than 90%, the answer is no, the "N" branch is taken and process 500 returns to step 502 and repeats step 502. If IR reflectance is less than 90%, the answer is yes, and the "Y" branch is taken and at step 506, computing device 115 can direct UV light emitter 308 to emit UV LED radiation 310 to activate self-cleaning glass portion of sealed glass portion 306 of sensor pod 202 as described above in relation to FIGS. 2 and 3. In this case, the UV LED radiation 310 can be emitted based on IR reflectance, determined environmental UV radiation and a schedule. Following this step process 500 ends.

Computing devices such as those discussed herein generally each include instructions executable by one or more computing devices such as those identified above, and for carrying out blocks or steps of processes described above. For example, process blocks discussed above may be embodied as computer-executable instructions.

Computer-executable instructions may be compiled or interpreted from computer programs created using a variety of programming languages and/or technologies, including, without limitation, and either alone or in combination, Java™, C, C++, Visual Basic, Java Script, Perl, HTML, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored in files and transmitted using a variety of computer-readable media. A file in a computing device is generally a collection of data stored on a computer readable medium, such as a storage medium, a random access memory, etc.

A computer-readable medium includes any medium that participates in providing data (e.g., instructions), which may be read by a computer. Such a medium may take many forms, including, but not limited to, non-volatile media, volatile media, etc. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

All terms used in the claims are intended to be given their plain and ordinary meanings as understood by those skilled in the art unless an explicit indication to the contrary in made herein. In particular, use of the singular articles such as "a," "the," "said," etc. should be read to recite one or more of the indicated elements unless a claim recites an explicit limitation to the contrary.

The term "exemplary" is used herein in the sense of signifying an example, e.g., a reference to an "exemplary widget" should be read as simply referring to an example of a widget.

The adverb "approximately" modifying a value or result means that a shape, structure, measurement, value, determination, calculation, etc. may deviate from an exact described geometry, distance, measurement, value, determination, calculation, etc., because of imperfections in materials, machining, manufacturing, sensor measurements, computations, processing time, communications time, etc.

In the drawings, the same reference numbers indicate the same elements. Further, some or all of these elements could be changed. With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

We claim:

1. A computer apparatus, programmed to:
   activate a self-cleaning glass surface by irradiating the self-cleaning glass surface with UV LED radiation based on a determined energy of environmental UV radiation and a schedule.

2. The apparatus of claim 1 wherein the UV LED radiation is further based on a determined optical state of the self-cleaning glass.

3. The apparatus of claim 2, further comprising: determining an optical state of the self-cleaning glass by determining an IR reflectance of the self-cleaning glass.

4. The apparatus of claim 1, wherein the UV LED radiation includes a wavelength 365 nanometers.

5. The apparatus of claim 4, further comprising: irradiate the self-cleaning glass surface with UV LED radiation having energy of greater than 1 $W/cm^2$.

6. The apparatus of claim 1, further comprising: determining the schedule based on expected environmental ultraviolet radiation.

7. The apparatus of claim 1, further comprising: determining external UV radiation energy based on $W*sec/cm^2$ of UV energy on the self-cleaning glass per time period.

8. The apparatus of claim 7, wherein the self-cleaning glass is coated with an optical UV coating.

9. The apparatus of claim 8, wherein the schedule includes less than ½ hour of UV LED radiation.

10. The apparatus of claim 9, wherein the less than ½ hour of UV LED radiation activates the self-cleaning glass surface for at least 2 to 5 hours.

* * * * *